United States Patent

Rizkalla et al.

[11] Patent Number: 5,854,167
[45] Date of Patent: Dec. 29, 1998

[54] ETHYLENE OXIDE CATALYST

[75] Inventors: Nabil Rizkalla, Rivervale; Rita Klein, Westwood; Stephen Bruce Milne, Wayne, all of N.J.

[73] Assignee: Scientific Design Company, Inc., Little Ferry, N.J.

[21] Appl. No.: 922,043

[22] Filed: Sep. 2, 1997

[51] Int. Cl.$^6$ .......................... B01J 27/02; B01J 27/055
[52] U.S. Cl. .................. 502/216; 502/208; 502/217; 502/218; 502/224; 502/227; 502/231; 502/344; 502/347; 502/348; 502/349
[58] Field of Search ..................... 502/208, 216, 502/217, 218, 224, 231, 227, 344, 347, 348, 349

[56] References Cited

U.S. PATENT DOCUMENTS

| | | |
|---|---|---|
| 3,702,259 | 11/1972 | Nielsen . |
| 3,888,889 | 6/1975 | Kolombos et al. . |
| 3,962,136 | 6/1976 | Nielsen et al. . |
| 4,007,135 | 2/1977 | Hayden et al. . |
| 4,766,105 | 8/1988 | Lauritzen . |
| 4,908,343 | 3/1990 | Bhasin . |
| 5,051,395 | 9/1991 | Mitchell et al. . |
| 5,057,481 | 10/1991 | Bhasin . |
| 5,102,848 | 4/1992 | Soo et al. . |
| 5,486,628 | 1/1996 | Kemp . |
| 5,504,052 | 4/1996 | Rizkalla et al. . |
| 5,646,087 | 7/1997 | Rizkalla et al. . |

FOREIGN PATENT DOCUMENTS 0266015   5/1988   European Pat. Off. .

*Primary Examiner*—Elizabeth D. Wood
*Attorney, Agent, or Firm*—William C. Long

[57] ABSTRACT

A silver catalyst for ethylene oxidation to ethylene oxide is provided containing a promoter combination consisting of an alkali metal component, a sulfur component, a germanium or tin component, and a fluorine component the catalyst being essentially free of rhenium and transition metal compounds.

5 Claims, No Drawings

ETHYLENE OXIDE CATALYST

BACKGROUND OF THE INVENTION

1. Field of the Invention

The present invention relates to a catalyst for the oxidation of ethylene to ethylene oxide consisting of silver, alkali metal such as cesium, a germanium or tin component, a sulfur component and a fluorine component deposited on a support such as alpha alumina and to the production of ethylene oxide using the catalyst. The catalyst is essentially free of rhenium or transition metal components.

2. Description of the Prior Art

Processes for the production of ethylene oxide involve the vapor phase oxidation of ethylene with molecular oxygen using a solid catalyst comprised of silver on a support such as alumina. There have been great efforts by many workers to improve the effectiveness and efficiency of the silver catalyst for producing ethylene oxide. U.S. Pat. No. 5,051,395 provides a comprehensive analysis of these efforts of prior workers.

Among the many prior teachings in this area is that of U.S. Pat. No. 4,007,135 (see also UK 1,491,447) which teaches variously silver catalysts for the production of ethylene and propylene oxides comprised of a promoting amount of copper, gold, magnesium, zinc, cadmium, mercury, strontium, calcium, niobium, tantalum, molybdenum, tungsten, chromium, vanadium, and/or preferably barium, in excess of any present in immobile form in the preformed support as impurities or cements (column 2, lines 1–15), silver catalysts for the production of propylene oxide comprising a promoting amount of at least one promoter selected from lithium, potassium, sodium, rubidium, cesium, copper, gold, magnesium, zinc, cadmium, strontium, calcium, niobium, tantalum, molybdenum, tungsten, chromium, vanadium and barium, in excess of any present in immobile form in the preformed support as impurities or cements (column 2, lines 16–34), as well as silver catalysts for producing ethylene oxide or propylene oxide comprising (a) a promoting amount of sodium, cesium, rubidium, and/or potassium, and (b) magnesium, strontium, calcium and/or preferably barium in a promoting amount (column 3, lines 5–8).

U.S. Pat. No. 5,057,481, and related 4,908,343 are concerned with silver ethylene oxide catalysts comprised of cesium and an oxyanion of a group 3b to 7b element.

U.S. Pat. No. 3,888,889 describes catalysts suitable for the oxidation of propylene to propylene oxide comprised of elemental silver modified by a compound of an element from Group 5b and 6b. Although the use of supports is mentioned, there are no examples. The use of cesium is not mentioned.

European Publication 0 266 015 deals with supported silver catalysts promoted with rhenium and a long list of possible copromoters.

U.S. Pat. 5,102,848 deals with catalysts suitable for the production of ethylene oxide comprising a silver impregnated support also having thereon at least one cation promoter such as cesium, and a promoter comprising (i) sulfate anion, (ii) fluoride anion, and (iii) oxyanion of an element of Group 3b to 6b inclusive of the Periodic Table. Possibly for purposes of comparison since it is outside the scope of catalyst claimed, the patent shows at columns 21 and 22 a catalyst No. 6 comprised of Ag/Cs/S/F on a support, the Cs amount being 1096 ppm.

U.S. Pat. No. 5,486,628 describes a silver catalyst promoted with alkali metal, rhenium and a rare earth or lanthanide component.

In the context of the bewildering and vast number of references, many of them contradictory, applicant has discovered a novel and improved catalyst for the production of ethylene oxide.

BRIEF DESCRIPTION OF THE INVENTION

The present invention relates to an improved supported silver ethylene oxide catalyst containing a promoter combination consisting of a critical amount of an alkali metal component, preferably cesium, together with a sulfur component, a germanium or tin component and a fluorine component and to the catalyst preparation and use; the catalyst is essentially free of rhenium and transition metal components.

As a result of recent studies we have discovered that catalysts prepared with Cs/S/F and germanium or tin outperformed standard catalysts prepared with cesium, sulfur (as sulfate), and fluorine (as fluoride) alone. In this case, catalysts promoted with germanium (as ammonium hexafluorogermanate) or tin (as tin bromide) yielded selectivities of 83.8% or higher without optimization of the elements. The remaining main group elements of group 14 exhibited dramatically lower selectivities compared to the standard cesium, sulfur, and fluorine benchmark of 83.3%.

Detailed Description

Preferred catalysts prepared in accordance with this invention contain up to about 30% by weight of silver, expressed as metal, deposited upon the surface and throughout the pores of a porous refractory support. Silver contents higher than 20% by weight of total catalyst are effective, but result in catalysts which are unnecessarily expensive. Silver contents, expressed as metal, of about 5–20% based on weight of total catalyst are preferred, while silver contents of 8–15% are especially preferred.

In addition to silver, the catalyst of the invention also contains a critical promoter combination consisting of certain amounts of alkali metal, sulfur, fluorine and germanium or tin. The critical amount of alkali metal promoter component is not more than 3000 ppm expressed as alkali metal based on the catalyst weight; preferably the catalyst contains 400–1500 ppm, more preferably 500–1000 ppm alkali metal based on the catalyst weight. Preferably the alkali metal is cesium although lithium, sodium, potassium, rubidium and mixtures can also be used. Impregnation procedures such as are described in U.S. Pat. No. 3,962,136 are advantageously employed for addition of the cesium component to the catalyst.

Necessary also for practice of the invention is the provision of sulfur as a promoting catalyst component. The sulfur component can be added to the catalyst support impregnating solution as sulfate, eg. cesium sulfate, ammonium sulfate, and the like. U.S. Pat. No. 4,766,105 describes the use of sulfur promoting agents, for example at column 10, lines 53–60, and this disclosure is incorporated herein by reference. The use of sulfur (expressed as the element) in amount of 5–300 ppm by weight more preferably 20–150 ppm by weight based on the weight of catalyst is essential in accordance with the invention.

The catalyst also contains a fluorine promoter in amount expressed as the element F of 10–1000 ppm, preferably 50–300 ppm by weight based on the catalyst as an essential component. Ammonium fluoride, alkali metal fluoride, and the like can be used.

The invention also requires a promoting amount of germanium or tin. The use of germanium or tin expressed as the element in the amount of 10–1000 ppm by weight based on the weight of the catalyst, more preferably 25–300 ppm, is essential in accordance with the invention. Germanium oxide, germanium chloride, germanium bromide, germanium iodide, tin fluoride, tin chloride, tin bromide, tin iodide, tin fluorophosphate, tin oxide and the like can be used.

The catalysts are made with supports prepared from porous refractory materials. Preferred supports include alumina, silica, silica-alumina or combinations thereof, charcoal, pumice, silicon carbide, magnesia, zirconia, and niobia. More preferred supports are those containing principally alpha-alumina, particularly those containing up to about 15 wt % silica.

Especially preferred supports have a porosity of about 0.1–0.9 cc/g and preferably about 0.2–0.7 cc/g. Preferred supports also have a relatively low surface area, i.e. about 0.2–5.0 $m^2/g$, preferably 0.4–2.0 $m^2/g$ and most preferably 0.5–1.3 $m^2/g$ as determined by the BET method. See J. Am. Chem. Soc. 60, 3098–16 (1938). Porosities are determined by the mercury porosimeter method; see Drake and Ritter, "Ind. Eng. Chem. anal. Ed.," 17, 787 (1945). Pore and pore diameter distributions are determined from the surface area and apparent porosity measurements.

For use in commercial ethylene oxide production applications, the supports are desirably formed into regularly shaped pellets, spheres, rings, etc. Desirably, the support particles may have "equivalent diameters" in the range from 3–10 mm and preferably in the range of 4–8 mm, which are usually compatible with the internal diameter of the tubes in which the catalyst is placed. "Equivalent diameter" is the diameter of a sphere having the same external surface (i.e. neglecting surface within the pores of the particle) to volume ratio as the support particles being employed.

Preferably, the silver is added to the support by immersion of the support into a silver/amine impregnating solution or by the incipient wetness technique. The silver containing liquid penetrates by absorption, capillary action and/or vacuum into the pores of the support. A single impregnation or a series of impregnations, with or without intermediate drying, may be used, depending in part upon the concentration of the silver salt in the solution. To obtain catalyst having silver contents within the preferred range, suitable impregnating solutions will generally contain from 5–50 wt % silver, expressed as metal. The exact concentrations employed, of course, will depend upon, among other factors, the desired silver content, the nature of the support, the viscosity of the liquid, and solubility of the silver compound.

Impregnation of the selected support is achieved in a conventional manner. The support material is placed in the silver solution until all of the solution is absorbed by the support. Preferably the quantity of the silver solution used to impregnate the porous support is no more than is necessary to fill the pore volume of the porous support.

The impregnating solution, as already indicated, is characterized as a silver/amine solution, preferably such as is fully described in U.S. Pat. No. 3,702,259 the disclosure of which is incorporated herein by reference. The impregnation procedures described in U.S. Pat. No. 3,962,136 are advantageously employed for the cesium component.

Known prior procedures of predeposition, co-deposition and postdeposition of the various promoters can be employed.

After impregnation, any excess impregnating solution is separated and the support impregnated with silver and the promoter or promoters is calcined or activated. In the most preferred practice of the invention, calcination is carried out as described in commonly assigned U.S. Pat. No. 5,504,052 granted Apr. 2, 1996 and copending application Ser. No. 08/587,281 filed Jan. 16, 1996 now U.S. Pat. No. 5,646,087 granted Jul. 8, 1997, the disclosures of which are incorporated herein by reference. The calcination is accomplished by heating the impregnated support, preferably at a gradual rate, to a temperature in the range 200°–500° C. for a time sufficient to convert the contained silver to silver metal and to decompose the organic materials and remove the same as volatiles.

The impregnated support is optionally maintained under an inert atmosphere while it is above 300° C. during the entire procedure. While not wishing to be bound by theory, it is believed that at temperatures of 300° C. and higher oxygen is absorbed in substantial quantities into the bulk of the silver where it has an adverse effect on the catalyst characteristics. Inert atmospheres which are optionally employed in the invention are those which are essentially free of oxygen.

An alternative method of calcination is to heat the catalyst in a stream of air at a temperature not exceeding 300° C., preferably not exceeding 250° C.

Catalysts prepared in accordance with the invention have improved performance, especially stability, for the production of ethylene oxide by the vapor phase oxidation of ethylene with molecular oxygen. These usually involve reaction temperatures of about 150° C. to 400° C., usually about 200° C. to 300° C., and reaction pressures in the range of from 0.5 to 35 bar. Reactant feed mixtures contain 0.5 to 20% ethylene and 3 to 15% oxygen, with the balance comprising comparatively inert materials including such substances as nitrogen, carbon dioxide, methane, ethane, argon and the like only a portion of the ethylene usually is reacted per pass over the catalyst and after separation of the desired ethylene oxide product and the removal of appropriate purge streams and carbon dioxide to prevent uncontrolled build up of inerts and/or by-products, unreacted materials are returned to the oxidation reactor.

A disadvantage of the prior art rhenium promoted catalysts has been the instability associated with such catalysts. In accordance with the present invention, the rhenium free catalysts have advantageously high selectivity and high stability.

The following examples illustrate the invention.

EXAMPLE 1

A silver solution was prepared using the following components (parts are by weight):

Silver oxide—834 parts

Oxalic acid—442 parts

Deionized water—2808 parts

Ethylene Diamine—415 parts

Silver oxide was mixed with water, at room temperature, followed by the gradual addition of the oxalic acid. The mixture was stirred for 15 minutes and at that point the color of the black suspension of silver oxide had changed to the gray/brown color of silver oxalate. The mixture was filtered and the solids were washed with 3 liters of deionized water.

A container which contained the washed solids was placed in an ice bath and stirred while ethylene diamine and water (as a 72%/28% mixture) were added slowly in order to maintain the reaction temperature lower than 33° C. After the addition of all the ethylene diamine water mixture the solution was filtered at room temperature. The clear filtrate was utilized as a silver/amine stock solution for the catalyst preparation.

The support used for the examples was obtained from Norton Company and was made primarily of alpha-alumina in the form of 5/16 inch cylinders. The support has a surface area of 0.65 m²/g, pore volume of 0.3 cc/g, and median pore diameter of 1.5. For the Examples, about 185 parts of the silver solution were mixed with varying amounts of:

1. CsOH solution, (8%Cs by weight in water),
2. ammonium fluoride, (3%F by weight in water)
3. ammonium hydrogen sulphate, (1%S by weight in water) and aqueous solution of the indicated Group 14 compound, the amounts of the promoter solutions being adjusted to give the promoter concentrations indicated in the tables.

The mixture of silver stock solution and promoter solutions was stirred to assure homogeneity, then added to 400 parts of the support. The wet catalyst was mixed for ten minutes and then calcined.

Calcination, the deposition of silver compound, was induced by heating the catalyst up to the decomposition temperature of the silver salt. This was achieved via heating in a furnace that has several heating zones in a controlled atmosphere. The catalyst was loaded on a moving belt that entered the furnace at ambient temperature. The temperature was gradually increased as the catalyst passed from one zone to the next. It was increased, up to 400° C., as the catalyst passed through seven heating zones. After the heating zones the belt passed through a cooling zone that gradually cooled the catalyst to a temperature lower than 100° C. The total residence time in the furnace was 22 minutes. Atmosphere of the furnace was controlled through use of nitrogen flow in the different heating zones. In some instances, as indicated in the following table the calcination was carried out with air.

The catalysts were tested in a stainless steel tube which was heated by a salt bath. A gas mixture containing 15% ethylene, 7% oxygen, and 78% inert, mainly nitrogen and carbon dioxide, was passed through the catalyst at 300 p.s.i.g., the temperature of the reaction was adjusted in order to obtain ethylene oxide productivity of 160 Kg per hour per m³ of catalyst and this temperature is given in the Table.

The results of the catalyst tests are summarized in Table 1.

TABLE 1

| Run | CS ppm | F ppm | S ppm | Metal ppm | Sel % | Temp °C. | metal cpd. |
|---|---|---|---|---|---|---|---|
| 1 | 330 | 67 | 34 | 0 | 81.5 | 219 | — |
| 2 | 611 | 0 | 34 | 0 | 82.4 | 237 | — |
| 3 | 606 | 80 | 34 | 0 | 82.8 | 238 | — |
| 4 | 668 | 180 | 34 | 0 | 83.2 | 253 | — |
| 5 | 641 | 181 | 34 | 72 Ge | 84.6 | 241 | $(NH_4)_2GeF_6$ |
| 6 | 622 | 0 | 34 | 125 Sn | 81.9 | 245 | $SnBr_2$ |
| 7 | 586 | 75 | 34 | 125 Sn | 83.8 | 236 | $SnBr_2$ |

In the above table, Runs 1–4 and 6 are comparative. The data demonstrate the substantially improved results achieved through the invention.

I claim:

1. A rhenium and transition metal free catalyst for the oxidation of ethylene to ethylene oxide comprised of silver on a solid support and containing a promoter combination consisting essentially of (1) an alkali metal component in amount not greater than 3000 ppm based on the weight of the catalyst, (2) a sulfur component in amount of 5–300 ppm based on the weight of the catalyst, (3) a germanium or tin component in amount of 10–1000 ppm based on the weight of the catalyst, and (4) a fluorine ; component in amount of 10–1000 ppm based on the weight of the catalyst.

2. The catalyst of claim 1 wherein the alkali metal component is cesium.

3. The catalyst of claim 2 wherein the cesium component is in amount of 400–800 ppm based on the weight of the catalyst.

4. The catalyst of claim 1 wherein the support is alpha alumina.

5. The catalyst of claim 1 comprised by weight of 5–20% silver.

* * * * *